US012784203B2

(12) United States Patent
Kamon

(10) Patent No.: US 12,784,203 B2
(45) Date of Patent: Nov. 3, 2026

(54) ENDOSCOPIC IMAGE PROCESSING DEVICE, ENDOSCOPIC IMAGE PROCESSING METHOD, AND ENDOSCOPE SYSTEM

(71) Applicant: FUJIFILM Corporation, Tokyo (JP)

(72) Inventor: Shumpei Kamon, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 160 days.

(21) Appl. No.: 18/633,487

(22) Filed: Apr. 11, 2024

(65) Prior Publication Data

US 2024/0257348 A1 Aug. 1, 2024

Related U.S. Application Data

(63) Continuation of application No. PCT/JP2022/033262, filed on Sep. 5, 2022.

(30) Foreign Application Priority Data

Oct. 20, 2021 (JP) ................................ 2021-171784

(51) Int. Cl.
*G06T 7/00* (2017.01)
*A61B 1/00* (2006.01)

(52) U.S. Cl.
CPC ...... *G06T 7/0012* (2013.01); *A61B 1/000094* (2022.02); *A61B 1/00045* (2013.01);
(Continued)

(58) Field of Classification Search
CPC ......... G06T 7/0012; G06T 2207/10068; G06T 2207/20081; G06T 2207/30092;
(Continued)

(56) References Cited

U.S. PATENT DOCUMENTS

2009/0074269 A1 3/2009 Nishimura et al.
2009/0196476 A1 8/2009 Inoue
(Continued)

FOREIGN PATENT DOCUMENTS

JP 2008036243 2/2008
JP 2017113184 6/2017
(Continued)

OTHER PUBLICATIONS

"International Search Report (Form PCT/ISA/210) of PCT/JP2022/033262," mailed on Nov. 15, 2022, with English translation thereof, pp. 1-5.

(Continued)

*Primary Examiner* — Tom Y Lu
(74) *Attorney, Agent, or Firm* — JCIPRNET

(57) ABSTRACT

There are provided an endoscopic image processing device, an endoscopic image processing method, and an endoscope system that can appropriately detect a region of interest from an endoscopic image. An endoscopic image processing device that processes an endoscopic image acquires the endoscopic image, recognizes a state of an organ as an examination target from the acquired endoscopic image, sets a detection criterion for a region of interest according to a recognition result of the state of the organ, and detects the region of interest from the endoscopic image on the basis of the set detection criterion.

24 Claims, 10 Drawing Sheets

(52) U.S. Cl.
CPC ............... *G06T 2207/10068* (2013.01); *G06T 2207/20081* (2013.01); *G06T 2207/30092* (2013.01)

(58) Field of Classification Search
CPC . G06T 7/00; A61B 1/000094; A61B 1/00045; A61B 1/00; A61B 1/000096; A61B 1/0005; A61B 1/045
See application file for complete search history.

(56) References Cited

U.S. PATENT DOCUMENTS

| | | | | |
|---|---|---|---|---|
| 2016/0147974 | A1 | 5/2016 | Sha et al. | |
| 2018/0249900 | A1* | 9/2018 | Imaizumi | G02B 23/2484 |
| 2018/0271412 | A1 | 9/2018 | Shigeta | |
| 2020/0294227 | A1* | 9/2020 | Usuda | A61B 1/000094 |
| 2021/0158528 | A1* | 5/2021 | Endo | G16H 30/40 |
| 2021/0192738 | A1 | 6/2021 | Meguro | |
| 2021/0343011 | A1 | 11/2021 | Kamon | |
| 2022/0000351 | A1* | 1/2022 | Yamada | A61B 1/00045 |
| 2022/0322974 | A1 | 10/2022 | Shigeta | |
| 2023/0162356 | A1* | 5/2023 | Horiuchi | A61B 1/00055 382/128 |

FOREIGN PATENT DOCUMENTS

| | | |
|---|---|---|
| JP | 2021100555 | 7/2021 |
| WO | 2007119297 | 10/2007 |
| WO | 2020162275 | 8/2020 |

OTHER PUBLICATIONS

"Written Opinion of the International Searching Authority (Form PCT/ISA/237) of PCT/JP2022/033262," mailed on Nov. 15, 2022, with English translation thereof, pp. 1-6.

"Notice of Reasons for Refusal of Japan Counterpart Application", issued on Aug. 5, 2026, with English translation thereof, p. 1-p. 5.

* cited by examiner

ENDOSCOPIC IMAGE PROCESSING DEVICE, ENDOSCOPIC IMAGE PROCESSING METHOD, AND ENDOSCOPE SYSTEM

CROSS-REFERENCE TO RELATED APPLICATIONS

The present application is a Continuation of PCT International Application No. PCT/JP2022/033262 filed on Sep. 5, 2022 claiming priority under 35 U.S.C § 119(a) to Japanese Patent Application No. 2021-171784 filed on Oct. 20, 2021. Each of the above applications is hereby expressly incorporated by reference, in its entirety, into the present application.

BACKGROUND OF THE INVENTION

1. Field of the Invention

The present invention relates to an endoscopic image processing device, an endoscopic image processing method, and an endoscope system, and particularly relates to an endoscopic image processing device, an endoscopic image processing method, and an endoscope system which process an image (endoscopic image) captured by an endoscope.

2. Description of the Related Art

As a technique for supporting examinations using an endoscope, a technique is known that automatically detects a region of interest such as a lesion from an endoscopic image and notifies the region of interest.

WO2007/119297A discloses a technique for detecting polyps as elevated lesions from endoscopic images, which detects elevated change regions from the endoscopic images and changes a detection criterion for a polyp depending on whether or not the detected elevated change regions are regions with a color tone change.

SUMMARY OF THE INVENTION

However, in WO2007/119297A, there is a disadvantage that the color tone change has to be detected for each of the detected elevated change regions and the detection criterion has to be set individually.

An embodiment of the technique of the present disclosure provides an endoscopic image processing device, an endoscopic image processing method, and an endoscope system that can appropriately detect a region of interest from an endoscopic image.

(1) An endoscopic image processing device that processes an endoscopic image, the endoscopic image processing device including a processor, in which the processor acquires the endoscopic image, recognizes a state of an organ as an examination target from the acquired endoscopic image, sets a detection criterion for a region of interest according to a recognition result of the state of the organ, and detects the region of interest from the endoscopic image on the basis of the set detection criterion.

(2) The endoscopic image processing device according to (1), in which the processor recognizes the state of the organ from the endoscopic image in which a specific region of the organ is imaged.

(3) The endoscopic image processing device according to (1), in which the processor recognizes the state of the organ from a plurality of endoscopic images in which different regions of the organ are imaged.

(4) The endoscopic image processing device according to (1), in which the endoscopic image used for recognizing the state of the organ is the endoscopic image in which a relatively wider range than the endoscopic image used for detecting the region of interest is imaged.

(5) The endoscopic image processing device according to any one of (1) to (4), in which the processor recognizes the state of the organ by recognizing a state regarding histological abnormalities in a mucous membrane from the endoscopic image.

(6) The endoscopic image processing device according to any one of (1) to (5), in which the processor acquires a plurality of endoscopic images captured in chronological order, recognizes the state of the organ from a first endoscopic image among the plurality of endoscopic images, and detects the region of interest from a second endoscopic image different from the first endoscopic image, among the plurality of endoscopic images.

(7) The endoscopic image processing device according to (6), in which the processor determines whether or not the recognition result of the state of the organ recognized from a plurality of first endoscopic images satisfies a specific condition, confirms the recognition result of the state of the organ in a case where the recognition result of the state of the organ recognized from the plurality of first endoscopic images satisfies the specific condition, and fixes setting of the detection criterion based on the confirmed recognition result of the state of the organ.

(8) The endoscopic image processing device according to (6) or (7), in which the second endoscopic image is the endoscopic image captured temporally later than the first endoscopic image.

(9) The endoscopic image processing device according to any one of (1) to (8), in which the processor displays information regarding the endoscopic image and the state of the organ recognized from the endoscopic image on a display device.

(10) The endoscopic image processing device according to any one of (1) to (9), in which the processor notifies of a detection result of the region of interest in a different mode according to setting of the detection criterion.

(11) The endoscopic image processing device according to (10), in which the processor notifies of the endoscopic image to be displayed on a display device by surrounding the detected region of interest with a frame, and displays the frame in a display aspect according to the setting of the detection criterion.

(12) The endoscopic image processing device according to any one of (1) to (11), in which the processor detects the region of interest from the endoscopic image using a trained model, and sets the trained model to be used for detecting the region of interest, according to the recognition result of the state of the organ.

(13) The endoscopic image processing device according to any one of (1) to (11), in which the processor detects region-of-interest candidates from the endoscopic image by calculating a confidence level indicating probability, detects the region-of-interest candidate of which the confidence level is equal to or greater than a threshold value, from among the detected region-of-interest candidates, as the region of interest, and sets the threshold value according to the recognition result of the state of the organ.

(14) The endoscopic image processing device according to (5), in which the processor recognizes the state of the organ by recognizing a state regarding inflammation and/or atrophy of the mucous membrane as the state regarding the histological abnormalities in the mucous membrane.

(15) The endoscopic image processing device according to (14), in which the processor recognizes a state regarding pylori infection of a stomach.

(16) The endoscopic image processing device according to (15), in which the processor recognizes uninfected, currently infected, and eradicated states as the state regarding the pylori infection of the stomach.

(17) The endoscopic image processing device according to (16), in which in a case where the recognition result of the state regarding the pylori infection of the stomach indicates the uninfected state, the processor sets the detection criterion relatively lower than in a case where the recognition result indicates the currently infected state and/or the eradicated state.

(18) The endoscopic image processing device according to (14), in which the processor recognizes a state regarding Barrett's esophagus of an esophagus.

(19) The endoscopic image processing device according to (14), in which the processor recognizes a state regarding an inflammatory bowel disease of a large intestine.

(20) The endoscopic image processing device according to any one of (1) to (18), in which the processor recognizes the state of the organ by dividing the state into three or more states, and sets the detection criterion according to the recognized state of the organ.

(21) The endoscopic image processing device according to any one of (1) to (20), in which the processor acquires information on a light source type, and sets the detection criterion according to the recognition result of the state of the organ and the light source type.

(22) An endoscopic image processing method of performing processing of detecting a region of interest from an endoscopic image using a trained model, the endoscopic image processing method including acquiring information on a state of an organ as an examination target; and setting the trained model to be used according to the state of the organ.

(23) An endoscopic image processing method of performing processing of detecting region-of-interest candidates from an endoscopic image by calculating a confidence level indicating probability, and detecting the region-of-interest candidate of which the confidence level is equal to or greater than a threshold value, from among the detected region-of-interest candidates, as a region of interest, the endoscopic image processing method including acquiring information on a state of an organ as an examination target; and setting the threshold value according to the state of the organ.

(24) An endoscope system including an endoscope; and the endoscopic image processing device according to any one of (1) to (21) that processes the endoscopic image captured by the endoscope.

According to the present invention, the region of interest can be detected from the endoscopic image appropriately.

DESCRIPTION OF THE PREFERRED EMBODIMENTS

Hereinafter, preferred embodiments of the present invention will be described in detail with reference to the accompanying drawings.

First Embodiment

Outline

In endoscopy, the appearance of a region of interest such as a lesion may differ greatly depending on a state of an organ as an examination target. For example, in gastric endoscopy, the appearance of a region of interest (for example, stomach cancer region) differs greatly depending on a state of *Helicobacter pylori* infection (hereinafter, referred to as "pylori infection") in the stomach. Therefore, in a case where a region of interest is automatically detected, in a case where detection is performed using the same detection criterion, a situation may arise in which the region of interest cannot be detected appropriately. For example, in a case of being uninfected with pylori, a region with erythema or dysmorphia is a region in which a cancer should be suspected, and is a detection target as the region of interest. On the other hand, in a case of being currently infected with pylori, even in a case where it is not a cancer, there may be findings such as erythema and dysmorphia. Therefore, in the case of being currently infected with pylori, these are no detection targets. In this manner, in a case where a region of interest is detected using the same detection criterion regardless of the state of the organ as the examination target, a situation may arise in which the region of interest cannot be detected appropriately.

Thus, in the endoscope system of the present embodiment, in a case of detecting a region of interest from an endoscopic image, the detection criterion is switched according to the state of the organ as the examination target. Thereby, the region of interest can be appropriately detected from the endoscopic image regardless of the state of the organ as the examination target.

[Configuration of Endoscope System]

Here, a case where the present invention is applied to an endoscope system that performs endoscopy for an upper digestive organ, particularly, gastric endoscopy will be described as an example. As mentioned above, in gastric endoscopy, the appearance of the region of interest differs greatly depending on the state of pylori infection in the stomach. Therefore, in the endoscope system of the present embodiment, the detection criterion is switched depending on the state of the pylori infection in the stomach, and the detection of the region of interest from the endoscopic image is performed.

[System Configuration]

Figure 1:
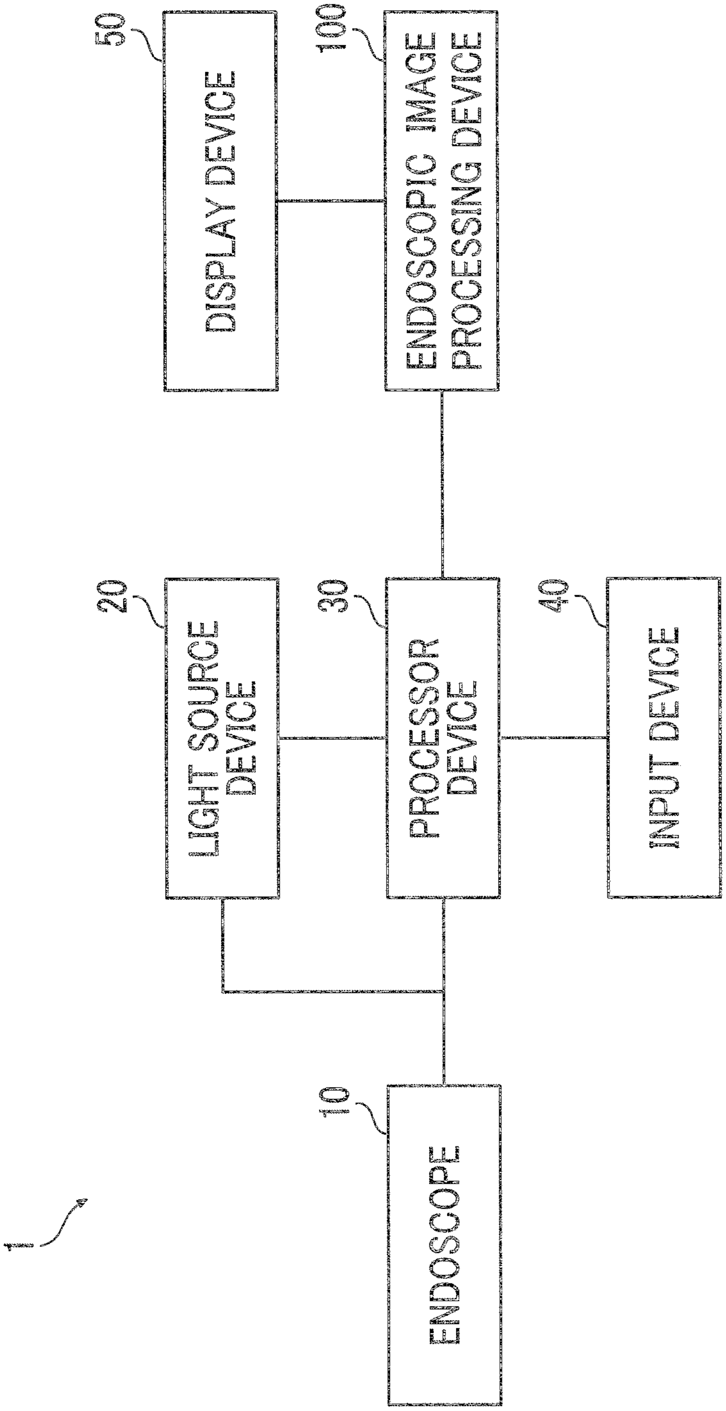
FIG. 1 is a diagram illustrating an outline of a system configuration of an endoscope system.

FIG. 1 is a diagram illustrating an outline of the system configuration of the endoscope system.

As illustrated in FIG. 1, an endoscope system 1 of the present embodiment includes an endoscope 10, a light source device 20, a processor device 30, an input device 40, a display device 50, an endoscopic image processing device 100, and the like. The endoscope 10 is electrically connected to the light source device 20 and the processor device 30. The light source device 20, the input device 40, and the endoscopic image processing device 100 are connected to the processor device 30. The display device 50 is connected to the endoscopic image processing device 100.

The endoscope system 1 of the present embodiment is configured as a system capable of an observation using special light (special light observation) in addition to an observation using normal white light (white light observation). In the special light observation, a narrow-band light observation is included. In the narrow-band light observation, a blue laser imaging observation (BLI observation), a narrow band imaging observation (NBI observation), a linked color imaging observation (LCI observation), and the like are included. Note that the special light observation itself is a well-known technique, so detailed description thereof will be omitted.

[Endoscope]

The endoscope 10 of the present embodiment is an electronic endoscope (flexible endoscope), particularly an electronic endoscope for an upper digestive organ. The electronic endoscope includes an operating part, an inserting part, a connecting part, and the like, and a subject is imaged using an imaging element built into a distal end of the inserting part. As the imaging element, a color image pickup element (for example, a color image pickup element using Complementary Metal Oxide Semiconductor (CMOS), Charge Coupled Device (CCD), or the like) having a predetermined filter array (for example, Bayer array) is used. Note that since the endoscope itself is well known, so detailed description thereof will be omitted. The endoscope 10 is electrically connected to the light source device 20 and the processor device 30 via the connecting part.

[Light Source Device]

The light source device 20 generates illumination light to be supplied to the endoscope 10. As described above, the endoscope system 1 of the present embodiment is configured as a system capable of the special light observation in addition to the normal white light observation. Therefore, the light source device 20 has a function of generating light (for example, narrow-band light) corresponding to the special light observation in addition to the normal white light. Note that, as described above, the special light observation itself is a well-known technique, so the description for the illumination light generation will be omitted. Switching of the type of light source is performed using, for example, a light source type switching button or the like provided for the operation of the endoscope 10.

[Processor Device]

The processor device 30 integrally controls the operation of the entire endoscope system. The processor device 30 includes, as a hardware configuration, a processor, a main storage unit, an auxiliary storage unit, and the like. For example, the processor is configured by a central processing unit (CPU) and the like. For example, the main storage unit is configured by a random-access memory (RAM) and the like. For example, the auxiliary storage unit is configured by a hard disk drive (HDD), a flash memory including a solid-state drive (SSD), or the like.

Figure 2:
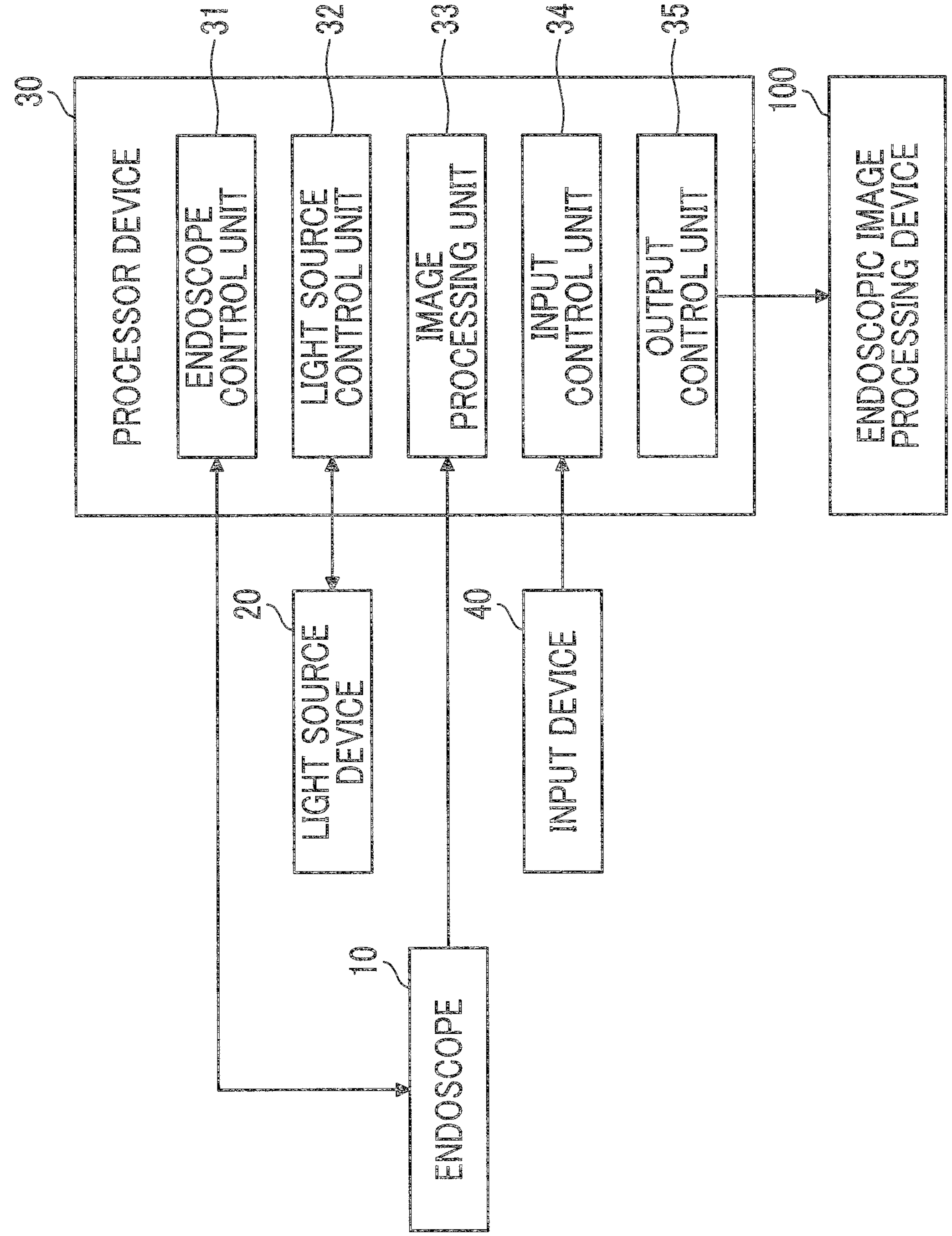
FIG. 2 is a block diagram of main functions of a processor device.

FIG. 2 is a block diagram of main functions of the processor device.

As illustrated in FIG. 2, the processor device 30 has functions of an endoscope control unit 31, a light source control unit 32, an image processing unit 33, an input control unit 34, an output control unit 35, and the like. Each function is realized by the processor executing a predetermined program. The auxiliary storage unit stores various programs executed by the processor, various kinds of data necessary for control, and the like.

The endoscope control unit 31 controls the endoscope 10. The control for the endoscope 10 includes imaging element drive control, air/water supply control, suction control, and the like.

The light source control unit 32 controls the light source device 20. The control for the light source device 20 includes light emission control for a light source, light source type switching control, and the like.

The image processing unit 33 performs various kinds of signal processing on signals output from the imaging element of the endoscope 10 to perform processing of generating a captured image.

The input control unit 34 performs processing of accepting an input of an operation and an input of various kinds of information via the input device 40.

The output control unit 35 controls an output of information to the endoscopic image processing device 100. The information to be output to the endoscopic image processing device 100 includes information and various kinds of instructional information input via the input device 40, in addition to the image (endoscopic image) captured by the endoscope. The various kinds of instructional information include instructional information (for example, light source type switching information or the like) of an operation unit of the endoscope 10.

[Input Device]

The input device 40 constitutes a user interface in the endoscope system 1 together with the display device 50. For example, the input device 40 is configured by a keyboard, a mouse, a foot switch, and the like. In addition, the input device 40 can include a touch panel, an audio input device, a gaze input device, and the like.

[Display Device]

The display device 50 is used not only to display the endoscopic image but also to display various kinds of information. For example, the display device 50 includes a liquid crystal display (LCD), an organic electroluminescence (EL) display (OLED), or the like. In addition, the display device 50 is configured by a projector, a head-mounted display, and the like.

[Endoscopic Image Processing Device]

The endoscopic image processing device 100 performs processing of detecting the region of interest such as a lesion part from the endoscopic image. In addition, processing of outputting the endoscopic image to the display device 50, including the detection result of the region of interest is performed.

The endoscopic image processing device 100 includes, as a hardware configuration, a processor, a main storage unit, an auxiliary storage unit, and the like. That is, the endoscopic image processing device 100 is configured with a computer. For example, the processor is configured by a CPU and the like. For example, the main storage unit is configured by RAM and the like. For example, the auxiliary storage unit is configured by a flash memory including SSD, a hard disk drive, or the like.

Figure 3:
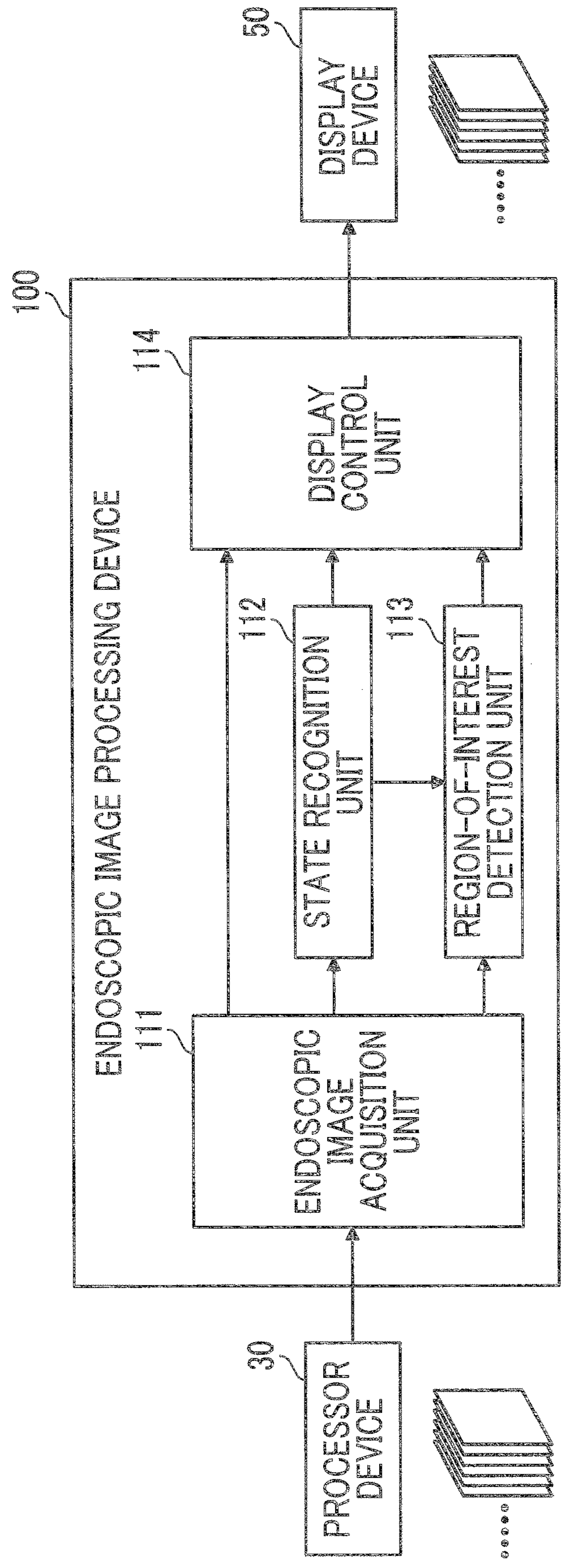
FIG. 3 is a block diagram of main functions of an endoscopic image processing device.

FIG. 3 is a block diagram of main functions of the endoscopic image processing device.

As illustrated in FIG. 3, the endoscopic image processing device 100 has functions of an endoscopic image acquisition unit 111, a state recognition unit 112, a region-of-interest detection unit 113, a display control unit 114, and the like. Each function is realized by the processor executing a predetermined program. The auxiliary storage unit stores programs executed by the processor, various kinds of data necessary for image process, and the like.

The endoscopic image acquisition unit 111 acquires an endoscopic image output from the processor device 30. Here, the processor device 30 outputs images (endoscopic images) captured by the endoscope 10 in chronological order. The endoscopic image acquisition unit 111 sequentially acquires endoscopic images output from the processor device 30 in chronological order.

The state recognition unit 112 performs processing of recognizing a state of the organ as the examination target from the endoscopic image acquired by the endoscopic image acquisition unit 111. As an example, in the present embodiment, processing of recognizing a pylori infection state of the stomach, that is, pylori positive (currently infected) and pylori negative (uninfected) from the endoscopic image of the stomach.

Figure 4:
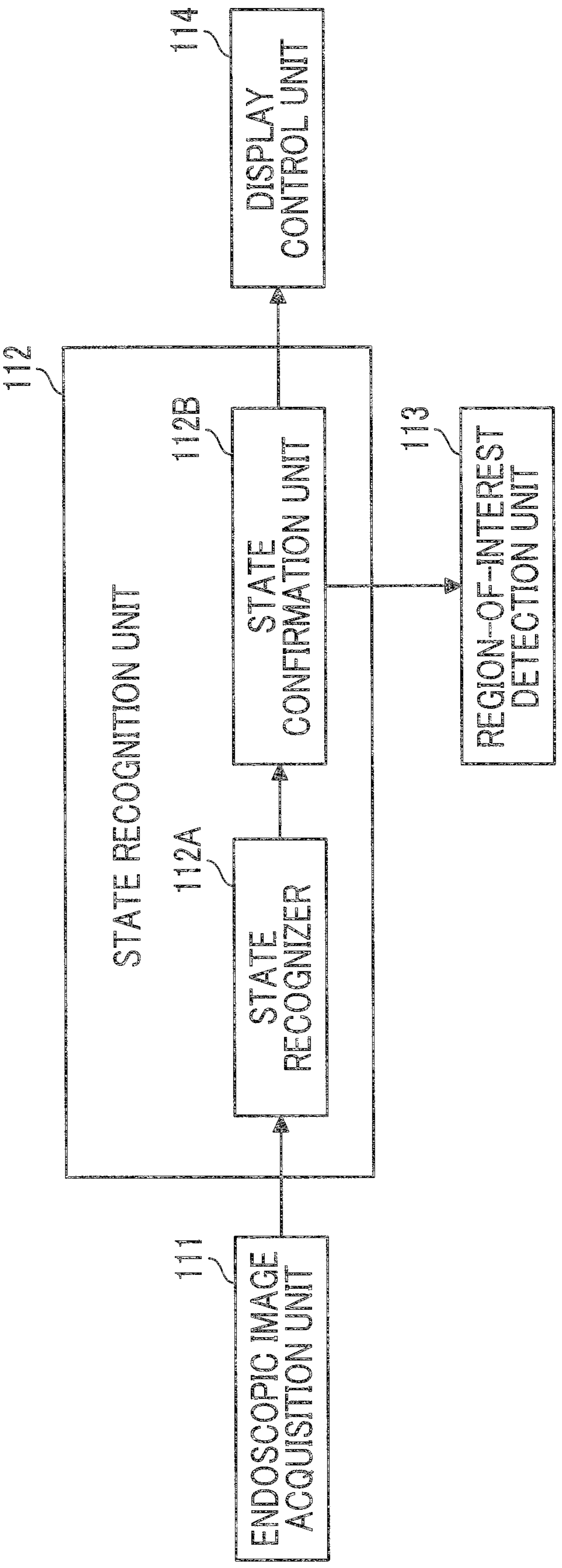
FIG. 4 is a block diagram of functions of a state recognition unit.

FIG. 4 is a block diagram of functions of the state recognition unit.

The state recognition unit 112 has functions of a state recognizer 112A that performs recognition processing and a state confirmation unit 112B that performs processing of confirming the recognition result.

The state recognizer 112A is configured, for example, by a trained model that has been trained to recognize a state of an organ from an endoscopic image. Specifically, each unit is configured by a trained model that has been trained using deep learning or a machine learning algorithm such as a neural network (NN), a convolutional neural network (CNN), AdaBoost, and random forest. As described above, in the present embodiment, in order to recognize the pylori infection state of the stomach, model training is performed using the endoscopic images of pylori positive and pylori negative as a training data set.

In general, the recognition of the status of pylori infection of the stomach using the endoscopic image can be determined using the presence or absence of atrophy of mucous membrane, inflammation, intestinal metaplasia and the like. The presence or absence of these can be recognized not only by changes in color tone, but also by visibility of blood vessels, dysmorphia in surface structure, and the like. In addition, histological abnormalities in the mucous membrane due to pylori infection are not local but spread over a wide range of the stomach. Therefore, it is preferable to recognize the abnormalities from an image in which a wide range of the stomach is imaged. In addition, even in the case of the pylori-positive stomach, it may have a structure locally similar to pylori negative mucous membrane. Therefore, in a case where an image close to the mucous membrane is recognized, there is a high possibility that an erroneous recognition result is output. Thus, in a case of constructing a model that recognizes the pylori infection state of the stomach, it is preferable to construct a model by taking these findings into consideration.

In a case where the recognition result of the state recognizer 112A satisfies a specific condition, the state confirmation unit 112B confirms the recognition result. That is, the state of the organ as the examination target is confirmed. In the present embodiment, the pylori infection state of the stomach is confirmed. Normally, the pylori infection state of the stomach does not change while the same subject is examined. In a case where a specific condition is satisfied, the recognition result is confirmed and the subsequent recognition processing is stopped. The state confirmation unit 112B determines whether or not confirmation of a recognition result is possible on the basis of a plurality of recognition results, and confirms the recognition result in a case where it is determined that the confirmation is possible. As an example, in the present embodiment, the recognition result is confirmed in a case where the same recognition result is consecutively obtained a predetermined number of times. Therefore, the state confirmation unit 112B of the present embodiment counts the number of times the same recognition result is obtained consecutively. In addition, it is determined whether or not the number of times has reached a predetermined number of times, and it is determined whether or not the confirmation of the recognition result is possible.

The region-of-interest detection unit 113 performs processing of detecting a region of interest such as a lesion from the endoscopic image acquired by the endoscopic image acquisition unit 111. As an example, in the present embodiment, processing of detecting a cancer-suspicious region (a region where cancer is suspected) from the endoscopic image of the stomach is performed. In the present embodiment, processing of detecting a region of interest from the endoscopic image is performed using a detector configured by a trained model.

Figure 5:
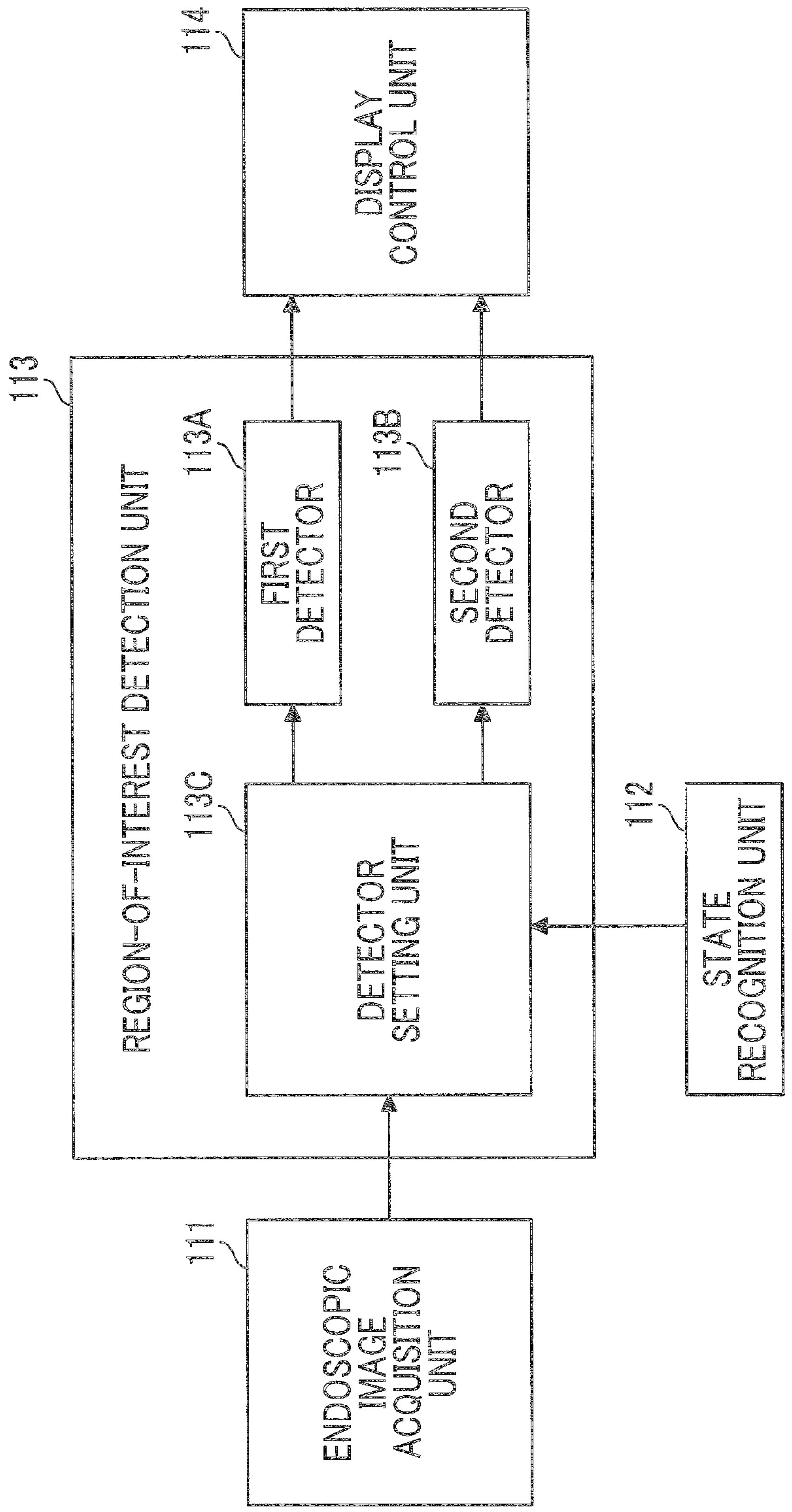
FIG. 5 is a block diagram of functions of a region-of-interest detection unit.

FIG. 5 is a block diagram of functions of the region-of-interest detection unit.

The region-of-interest detection unit 113 has a first detector 113A and a second detector 113B, and performs processing of detecting a region of interest using the detector set by a detector setting unit 113C.

The first detector 113A is a detector compatible with the examination for pylori-positive stomach. Specifically, the detector is a detector configured by a trained model that has been trained using endoscopic images of pylori-positive stomachs. Thus, favorable detection results can be obtained for pylori-positive stomachs.

On the other hand, the second detector 113B is a detector compatible with the examination for pylori-negative stomach. Specifically, the detector is a detector configured by a trained model that has been trained using endoscopic images of pylori-negative stomachs. Thus, favorable detection results can be obtained for pylori-negative stomachs.

Note that, similar to the state recognizer 112A of the state recognition unit 112, the first detector 113A and the second detector 113B are configured by a trained model that has been trained using deep learning or a machine learning algorithm such as a neural network, a convolutional neural network, AdaBoost, and random forest.

The detector setting unit 113C sets the detector to be used according to the recognition result of the pylori infection state by the state recognition unit 112. Specifically, in a case where the recognition result by the state recognition unit 112 indicates the pylori positive, the first detector 113A is selected and set. On the other hand, in a case where the recognition result by the state recognition unit 112 indicates the pylori negative, the second detector 113B is selected and set. In the present embodiment, the setting of the detector by the detector setting unit 113C is an example of setting a detection criterion for the region of interest.

The display control unit 114 controls display of the display device 50. The display control unit 114 displays the endoscopic image on the display device 50. In addition, in a case of detecting the region of interest, the display control unit 114 displays the detection result on the display device 50. Further, in a case of detecting the region of interest, the display control unit 114 displays the recognition result of the state of the organ on the display device 50.

Figure 6:
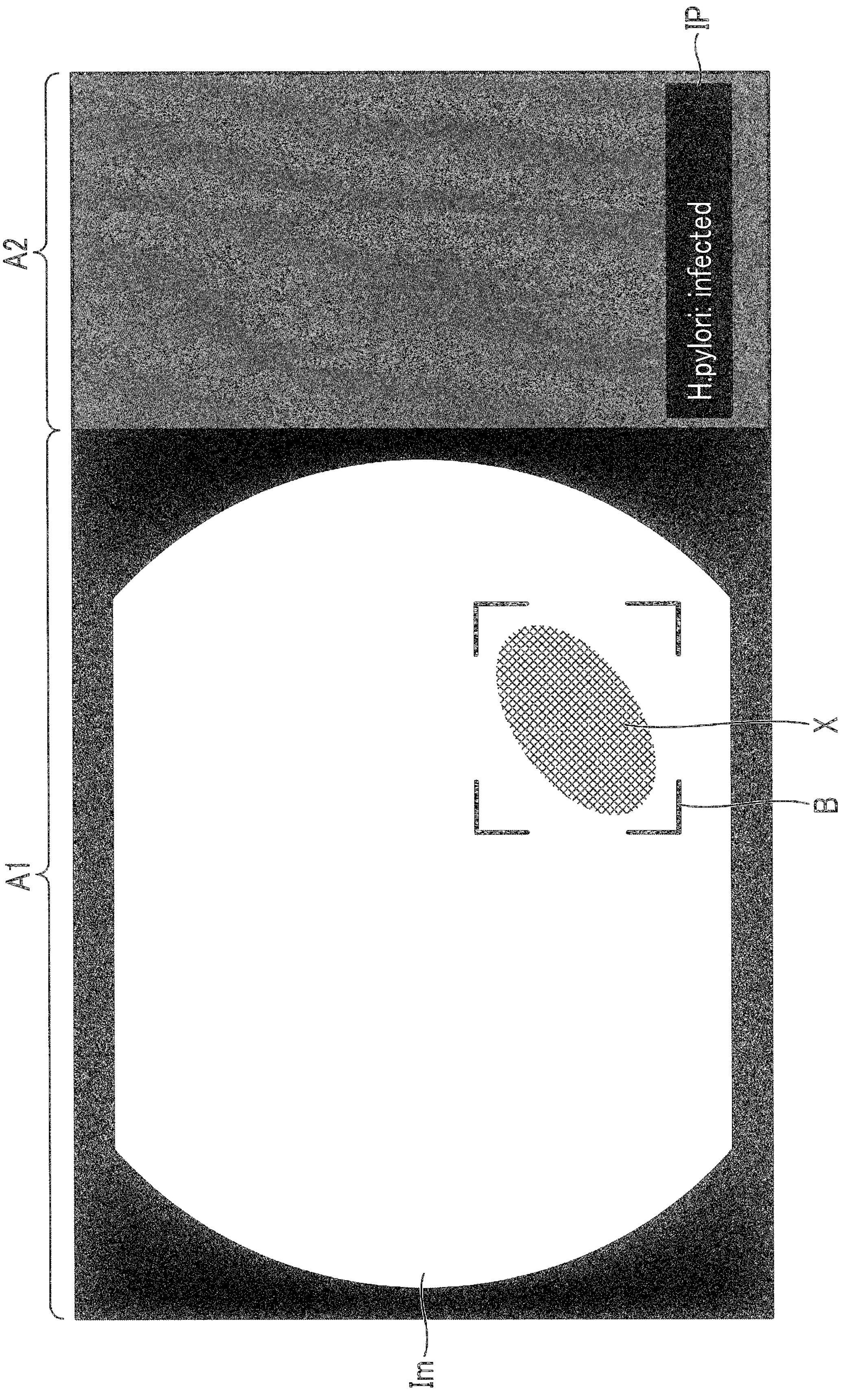
FIG. 6 is a diagram illustrating an example of display of a display device.
Figure 7:
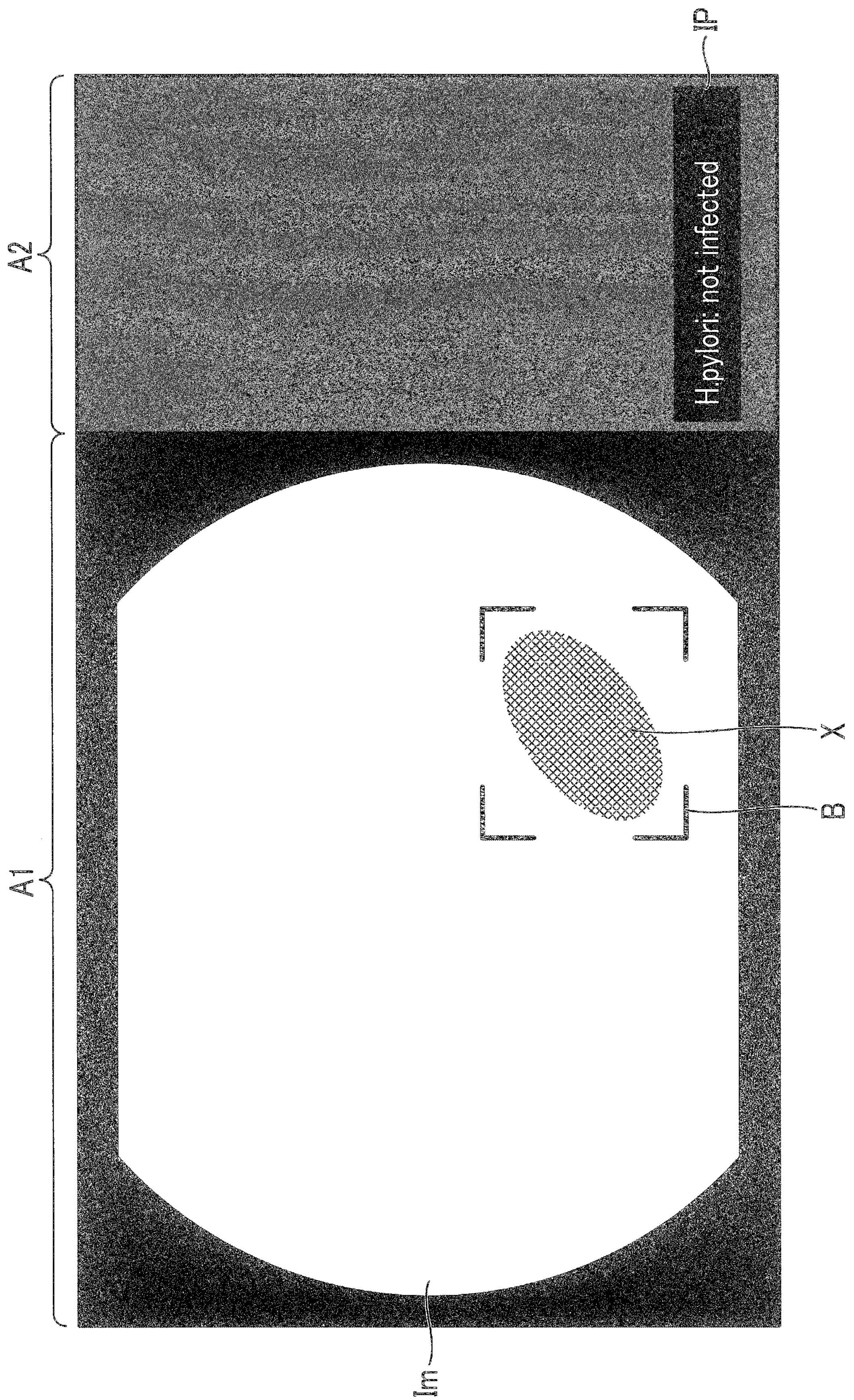
FIG. 7 is a diagram illustrating an example of display of the display device.

FIGS. 6 and 7 are diagrams illustrating an example of the display of the display device. FIGS. 6 and 7 illustrate an example of the display in the case of a so-called wide monitor. FIG. 6 illustrates an example of the display in a case of pylori positive. FIG. 7 illustrates an example of the display in a case of pylori negative.

As illustrated in FIGS. 6 and 7, a main display region A1 and a secondary display region A2 are set in the screen. The main display region A1 is a region where an endoscopic image Im is displayed. The endoscopic image Im is displayed in the main display region A1 in a predetermined display aspect. In the present embodiment, the endoscopic image Im is displayed within a circle with the top and bottom cut out. The secondary display region A2 is a so-called margin region, and is used to display various kinds of information such as setting information and captured static images.

In a case of performing the detection of the region of interest, in a case where a region of interest X is detected from the endoscopic image Im displayed in the main display region A1, the display control unit 114 displays a detection box B by superimposing the detection box on the endoscopic image Im. The detection box B is composed of a rectangular frame with only the corner portions displayed, and is displayed to surround the region of interest X. Therefore, the detection box B is displayed in a size corresponding to the size of the region of interest X. In addition, the detection box B is displayed in a predetermined color (for example, green). The detection box B is an example of a frame.

In addition, in a case where the state recognition unit 112 recognizes the state of the organ as the examination target, the display control unit 114 displays information IP on the recognition result in the secondary display region A2. In the present embodiment, the recognition result of the pylori infection state of the stomach is displayed. As an example, as illustrated in FIG. 6, in the case of the pylori positive, "*H. pylori*: infected" is displayed. On the other hand, in the case of the pylori negative, "*H. pylori*: not infected" is displayed as illustrated in FIG. 7. By checking this display, it is possible to check the pylori infection state of the stomach, and at the same time, it is possible to check which detector is being used to perform the detection processing. In the present embodiment, the information IP on the recognition result is an example of information regarding the state of the organ recognized from the endoscopic image.

[Operation of Endoscopic Image Processing Device]

Hereinafter, the operation of the endoscopic image processing device 100 will be described using a case of performing gastric endoscopy as an example.

Figure 8:
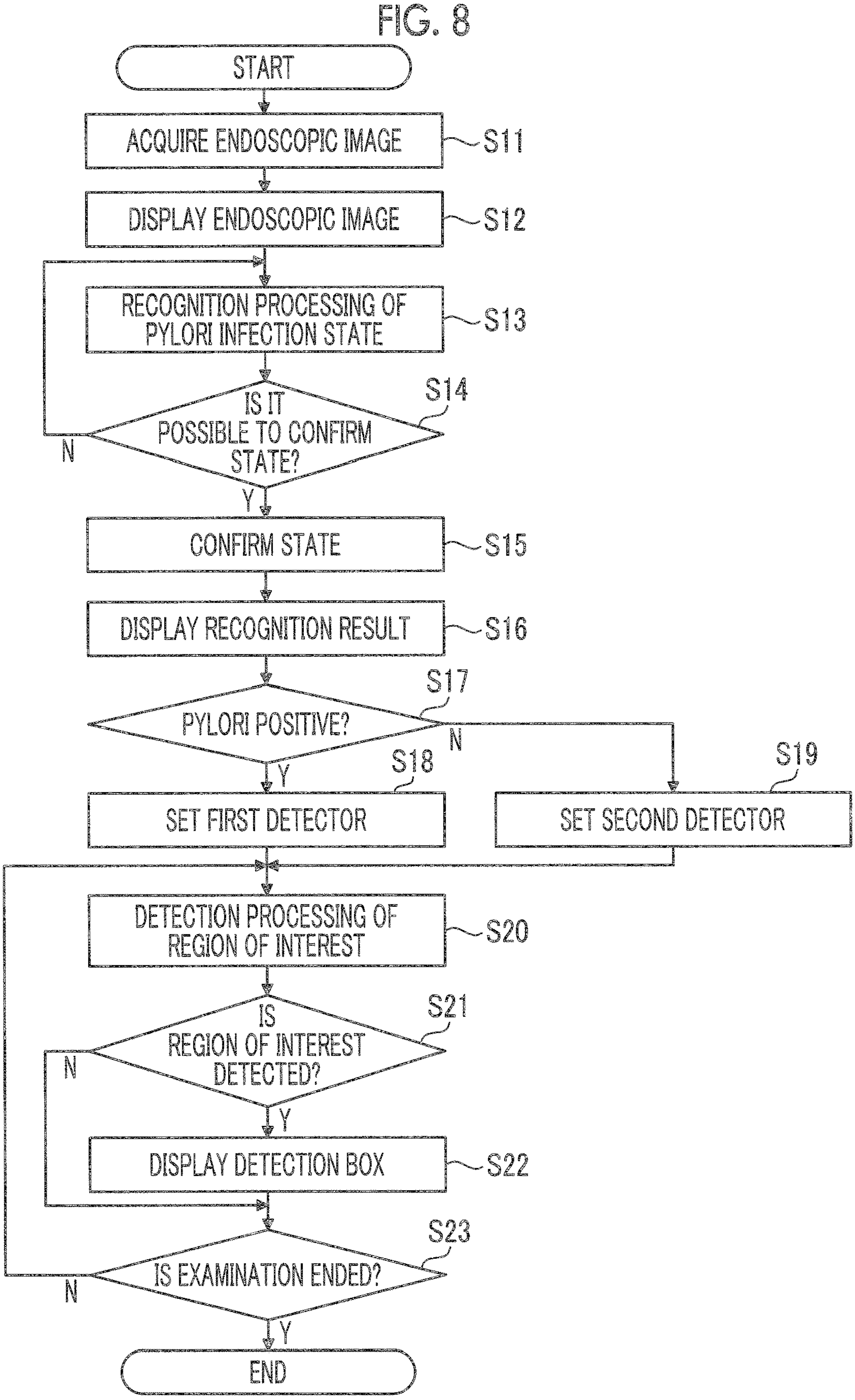
FIG. 8 is a flowchart illustrating a procedure of processing of detecting a region of interest from an endoscopic image.

FIG. 8 is a flowchart illustrating a procedure of processing of detecting the region of interest from the endoscopic image.

In a case where an examination starts, the images (endoscopic images) captured in chronological order by the endoscope 10 are sequentially output from the processor device 30 and taken into the endoscopic image processing device 100. That is, time-series endoscopic images are sequentially acquired (Step S11). Note that the actual examination (observation) starts after predetermined cleaning is performed on the stomach.

The acquired endoscopic image is displayed on the display device 50 (Step S12). The endoscopic image processing device 100 displays the endoscopic image Im in the main display region A1 set on the screen (refer to FIGS. 6 and 7).

In a case where the endoscopic image is acquired, recognition processing of the pylori infection state is performed on the acquired endoscopic image (Step S13). The recognition processing is sequentially performed on each of the endoscopic images acquired in chronological order.

In a case where the recognition processing is performed, it is determined whether or not the pylori infection state of the subject can be confirmed from the recognition processing result (Step S14). The determination is performed on the basis of a plurality of recognition results. In the present embodiment, the determination is performed depending on whether or not the same recognition result is consecutively obtained a predetermined number of times. In a case where the same recognition result is consecutively obtained a predetermined number of times, it is determined that the pylori infection state can be confirmed.

In a case where it is determined that the pylori infection state can be confirmed, the pylori infection state is confirmed (Step S15). That is, the pylori positive or the pylori negative is confirmed.

In a case where the pylori infection state is confirmed, the recognition result is displayed on the display device 50 (Step S16). That is, the recognized pylori infection state is displayed (refer to FIGS. 6 and 7). The recognition result is displayed in the secondary display region A2 of the screen.

In addition, in a case where the pylori infection state is confirmed, it is determined whether or not the confirmed recognition result is the pylori positive (Step S17). Then, a detector to be used to detect the region of interest is set on the basis of the determination result thereof. Specifically, in a case where the confirmed recognition result is the pylori positive, the detector to be used is set to the first detector 113A (Step S18). On the other hand, in a case where the confirmed recognition result is the pylori negative, the detector to be used is set to the second detector 113B (Step S19).

After the detector to be used is set, the detection processing of the region of interest is performed using the set detector (Step S20). Specifically, in the case of the pylori positive, the detection processing of the region of interest from the endoscopic image is performed using the first detector 113A. In addition, in the case of the pylori negative, the detection processing of the region of interest from the endoscopic image is performed using the second detector 113B. The detection processing is sequentially performed on each of the endoscopic images acquired in chronological order. Then, it is determined whether or not the region of interest is detected for each time of detection processing (Step S21).

In a case where the region of interest is detected, the detection box B is displayed by being superimposed on the endoscopic image Im that is being displayed on the display device 50 (Step S22). The detection box B is displayed to surround the detected region of interest X (refer to FIGS. 6 and 7).

Then, it is determined whether or not the examination is ended (Step S23). In a case where the examination is ended, the processing is ended. In a case where the examination is continuing, the detection processing of the region of interest from the endoscopic image is continued (Step S20).

As described above, according to the endoscopic image processing device 100 of the present embodiment, in a case where the region of interest is detected from the endoscopic image, the detector to be used can be switched depending on the pylori infection state of the stomach. Accordingly, the region of interest can be detected appropriately.

Modification Example

[Modification Example of Recognition of Pylori Infection State of Stomach]

Regarding the pylori infection state of the stomach recognized from the endoscopic image, in addition to the pylori positive and the pylori negative, a state after pylori eradication can also be recognized. In this case, detectors according to respective recognition results are prepared. That is, a detector (first detector) to be used in the case of the pylori positive (currently infected), a detector (second detector) to be used in the case of the pylori negative (uninfected), and a detector (third detector) to be used in the case after the pylori eradication (eradicated) are prepared. During the examination, the detector to be used is set according to the recognition result of the pylori infection state of the stomach, and the detection processing of the region of interest is performed. That is, in a case where the recognition result indicates the pylori positive, the first detector is selected, and the detection processing of the region of interest is performed. In addition, in a case where the recognition result indicates the pylori negative, the second detector is selected, and the detection processing of the region of interest is performed. In addition, in a case where the recognition result indicates a state after the pylori eradication, the third detector is selected, and the detection processing of the region of interest is performed. Accordingly, the region of interest can be detected more appropriately.

Note that, in a case where two states of the pylori positive and the pylori negative are recognized as the pylori infection state of the stomach, a configuration can be adopted in which the state after the pylori eradication is recognized as one of the two states.

[Modification Example of Recognition of State of Stomach]

In the embodiment described above, in the gastric endoscopy, an example has been described in which the pylori infection state of the stomach is recognized and the detector to be used is switched according to the recognition result thereof. The state of the stomach to be recognized is not limited to the pylori infection state. A configuration can be adopted in which a state of the stomach is recognized and a detector to be used is switched according to the result thereof. In particular, histological abnormalities in the mucous membrane have a large effect on the detection of the lesion part. Thus, a configuration can be adopted in which a state regarding the histological abnormalities in the mucous membrane is recognized and a detector to be used is switched according to the recognition result thereof. As the state regarding the histological abnormalities in the mucous membrane, states regarding inflammation and/or atrophy of the mucous membrane are exemplified. By recognizing these states and switching the detector to be used according to the recognition result thereof, it becomes possible to detect the region of interest appropriately. In this case, the state can be recognized by being divided into three or more states. In addition, in this case, a model constituting the detector is trained using an image group according to the target to be recognized.

[Modification Example of Recognition Method of State of Stomach]

In the embodiment described above, the pylori infection state of the stomach is recognized from the endoscopic image of the stomach by using a machine-learned trained model, but the method of recognizing the state of the stomach, including the pylori infection state, is not limited thereto. The state of the stomach may be recognized using other methods.

In addition, the endoscopic image processing device 100 can be configured to acquire information on the state of the stomach by receiving an input of the information on the state of the stomach from the outside. For example, a configuration can be adopted in which, as the patient information, information on the pylori infection state of the stomach of a person to be examined is acquired by being input from the outside. The information can also be manually input by a user via the input device 40. In addition, a configuration can be adopted in which the information can be automatically input by being included in other input information.

In a case where the state of the stomach is recognized from the endoscopic image, a configuration can be adopted in which the state of the stomach is recognized from the endoscopic image in which a specific region of the stomach is imaged. That is, a configuration can be adopted in which the recognition is performed from an image in which a region where a target state is easily recognized is imaged. For example, for the pylori infection state, a configuration can be adopted in which recognition is performed from an image in which the lesser curvature of the stomach or the upper region of the stomach in a case where the stomach is divided into upper and lower parts is imaged. Note that, as described above, regarding the pylori infection, since the histological abnormalities in the mucous membrane due to the pylori infection spread over a wide range of the stomach, it is preferable to perform the recognition from an image in which a wide range of the stomach is imaged. In this case, in addition to a method of performing recognition from one image in which a wide range is imaged, a method or performing recognition from a plurality of endoscopic images in which different regions are imaged can be adopted. That is, a method of performing recognition from a plurality of images in which a target region is divided and imaged can be adopted. A model constituting a detector can be trained using an image group according to the recognition method.

In a case where the state of the stomach is recognized from the image in which a specific range is imaged, a configuration can be adopted in which a specific range is recognized from the endoscopic image and the recognition processing of the state is performed. For example, in a case where the state of the stomach is recognized from the lesser curvature of the lower gastric body, a configuration can be adopted in which the lesser curvature of the lower gastric body is recognized and the state of the stomach is recognized from the image of the recognized lesser curvature of the lower gastric body.

[Regarding Confirmation Processing of Recognition Result]

In the embodiment described above, in a case where a specific condition is satisfied, the recognition result is confirmed and the subsequent recognition processing is stopped. However, a configuration can be adopted in which the recognition processing is constantly executed and the detector to be used is dynamically changed. For example, in a case where the detector is switched according to the locally changing state, the region of interest can be detected appropriately by constantly executing the recognition processing and dynamically switching the detector to be used. On the other hand, in a case of recognizing the state that does not change locally, such as the pylori infection state, it is preferable to perform processing of confirming the recognition result, then to stop the recognition processing, and to fix the detector to be used. This is because the state may not be recognized appropriately depending on the image. For example, in a case where the mucous membrane cannot be imaged due to factors such as water fog or blur, it is difficult to determine the state of the mucous membrane. Therefore, in a case of recognizing the state that does not change locally, by confirming the state early, subsequent erroneous recognition can be effectively prevented. In addition, accordingly, the region of interest can be detected appropriately.

In addition, the conditions for confirming the recognition result are not limited to those described in the above-described embodiment. The conditions can be set appropriately depending on the target to be recognized. For example, a configuration may be adopted in which the recognition result is confirmed in a case where the same detection result is obtained at a certain rate or more.

In addition, in the embodiment described above, the processing of detecting the region of interest starts after the recognition result of the state of the stomach is confirmed, but a configuration of detecting the region of interest in parallel with the recognition of the state of the stomach can be adopted. In this case, the detection of the region of interest is performed using a predetermined detector until the recognition result of the state of the stomach is confirmed. In addition, a detector to be used in a case where the state of the organ has not been confirmed may be prepared, and the detector may be used to detect the region of interest while the state of the organ is not confirmed.

[Relationship Between Recognition of State of Stomach and Detection of Region of Interest]

As described above, it is preferable to recognize the pylori infection from the image in which a wide range of the stomach is imaged. Therefore, it is preferable that the endoscopic image for recognizing the state of the stomach is an image in which a relatively wider range than the endoscopic image for detecting the region of interest is imaged. The wide-range image includes not only a single image captured of a wide range but also images captured of a wide range divided into a plurality of parts.

In addition, in chronological order, it is preferable that the detection of the region of interest is performed after the state of the stomach is recognized and the detector to be used is decided. Thus, it is preferable that the endoscopic image for detecting the region of interest is an image captured temporally later than the endoscopic image for recognizing the state of the stomach. In this case, the endoscopic image for recognizing the state of the stomach is an example of a first endoscopic image, and the endoscopic image for detecting the region of interest is an example of a second endoscopic image.

[Modification Example of Notification Method of Recognition Result]

In the embodiment described above, the information on the recognition result of the pylori infection state of the stomach is displayed on the display device 50, but the method of notifying of the recognition result is not limited thereto. For example, a configuration can be adopted in which the recognition result is notified by displaying an icon corresponding to the recognition result on the display device.

In addition, as in the above-described embodiment, in a case where the region of interest is detected, in a case of notifying of the detection result using a detection box, the recognition result may be notified by changing the display aspect of the detection box according to the recognition result. For example, the recognition result may be notified by changing the color of the detection box according to the recognition result. As an example, in the case of the pylori positive (currently infected), the detection box is displayed in green, and in the case of the pylori negative (uninfected), the detection box is displayed in red. In a case of recognizing also the state after pylori eradication (eradicated), for example, the detection box is displayed in blue. In addition, the recognition result may be notified by changing the shape of the detection box or changing the blinking state of the display according to the recognition result. Note that, in a case where the recognition result is notified by the colors or the like of the detection box in this manner, displaying the information on the recognition result in the secondary display region A2 can be omitted.

In addition, in a case of making a notification, a configuration can be adopted in which the notification is made in combination with audio such as a notification sound.

By notifying of the recognition result, the user can ascertain which detector is operating. Accordingly, the user can check whether or not an incorrect detector is being used.

Note that it is preferable that the detector to be used is configured to be manually switched. Accordingly, in a case where it is determined from the notification result that an incorrect detector has been selected, it is possible to switch to the correct detector.

[Regarding Application to Examination for Other Organs]

In the embodiment described above, a case where the examination for the stomach is performed is exemplified, but the application of the present invention is not limited thereto. Hereinafter, a case in which other organs are examined will be described.

(1) Examination for Esophagus

Regarding the esophagus, the type of cancer that develops differs depending on whether the mucous membrane is squamous epithelium or columnar epithelium (Barrett's esophagus). In the case of squamous epithelium that is a normal esophagus, it is necessary to pick out regions with erythema (which appear brownish in image enhanced endoscopy (IEE) such as NBI and BLI) from the faded squamous epithelium. On the other hand, in the case of Barrett's esophagus, it is necessary to pick out dysmorphia in the blood vessels and surface structure from the overall brownish appearance in the image enhanced endoscopy. In this manner, regarding the esophagus as well, the appearance of the region of interest (for example, a cancer-suspicious region) differs depending on the state of the esophagus, particularly the state of the histological abnormalities in the mucous membrane. Therefore, in the case of the examination for the esophagus as well, it is preferable to recognize the state of the esophagus in a case of detecting the region of interest, and to switch the detection criterion according to the recognition result thereof. As an example, whether the state of the mucous membrane of the esophagus is squamous epithelium or columnar epithelium is recognized, and the detector to be used is switched according to the recognition result thereof. That is, in a case where the state of the mucous membrane of the esophagus is squamous epithelium, the detection processing of the region of interest is performed using the detector compatible with the squamous epithelium. In addition, in a case where the state of the mucous membrane of the esophagus is columnar epithelium, the detection processing of the region of interest is performed using the detector compatible with the columnar epithelium. Alternatively, whether or not the state of the mucous membrane of the esophagus is columnar epithelium is recognized, and the detector to be used is switched according to the recognition result thereof. That is, in a case where the state of the mucous membrane of the esophagus is columnar epithelium, the detection processing of the region of interest is performed using the detector compatible with the columnar epithelium. On the other hand, in a case where the state of the mucous membrane of the esophagus is not columnar epithelium, the state is considered to be the normal esophagus, and the detection processing of the region of interest is performed using the detector compatible with the normal esophagus. Accordingly, the region of interest can be detected appropriately from the endoscopic image of the esophagus.

(2) Examination for Large Intestine

Regarding the large intestine, in a case of detecting polyps from a normal large intestine, hyperplastic polyps, adenomas, and the like are the detection targets in many cases. On the other hand, in the case of inflammatory bowel diseases (IBD) such as ulcerative colitis and Crohn's disease, inflammatory polyps, submucosal tumors, and the like occur frequently. The inflammatory polyps, submucosal tumors, and the like are all elevated structures, but the image features of the surfaces are significantly different. Therefore, in the case of the examination for the large intestine as well, it is preferable to recognize the state of the large intestine in a case of detecting the region of interest, and to switch the detection criterion according to the recognition result thereof. As an example, whether or not the state of the large intestine has inflammatory bowel disease is recognized, and the detector to be used is switched according to the recognition result thereof. That is, in the case of the large intestine having the inflammatory bowel disease, the detection processing of the region of interest is performed using the detector compatible with a case of having the inflammatory bowel disease. On the other hand, in the case of the large intestine not having the inflammatory bowel disease, the large intestine is considered to be the normal large intestine, and the detection processing of the region of interest is performed using the detector compatible with the normal large intestine. Accordingly, the region of interest can be detected appropriately from the endoscopic image of the large intestine.

Note that, similar to the pylori infection state of the stomach, the state of the inflammatory bowel disease does not change while the same subject is examined. Therefore, in the recognition processing, in a case where a specific condition is satisfied, the recognition result can be confirmed.

(3) Examination for Other Organs

Similarly, in a case of examining other organs, in a case where the image features of the region of interest change depending on the state of the organ, the function of detecting the region of interest appropriately can be realized by recognizing the state of the organ and switching the detector to be used according to the recognition result thereof.

Note that each modification example described for the examination for the stomach can also be appropriately applied to the case of examining other organs.

[Case where Light Source Type can be Switched]

As in the endoscope system 1 of the present embodiment, in a case where an observation in which the light source type is changed is possible, a configuration can be adopted in which information on the light source type being selected is acquired and the detector is switched for each light source type. Specifically, in a case where the white light observation and the special light observation are possible, a detector corresponding to the recognition result of the organ is prepared for each observation mode. For example, in the endoscope system, it is assumed that white light observation, BLI observation, and LCI observation are selectively possible. In this case, a detector to be used in a case of the pylori positive in the white light observation, a detector to be used in a case of the pylori negative in the white light observation, a detector to be used in a case where the pylori positive in the BLI observation, a detector to be used in a case of the pylori negative in the BLI observation, a detector to be used in a case of the pylori positive in the LCI observation, and a detector to be used in a case of the pylori negative in the LCI observation are prepared. Then, in each observation mode, the detector to be used is switched according to the recognition result of the pylori infection state of the stomach. Accordingly, the region of interest can be detected appropriately from the endoscopic image regardless of the light source type.

Second Embodiment

In the embodiment described above, the detection criterion is switched by switching the detector to be used according to the recognition result, but the method of changing the detection criterion is not limited thereto. In the present embodiment, a method of changing the detection criterion without changing the detector will be described.

Note that the configuration other than changing the detection criterion for the region of interest is the same as the endoscopic image processing device of the first embodiment. Therefore, in the following, only the functions of the region-of-interest detection unit included in the endoscopic image processing device of the present embodiment will be described.

Figure 9:
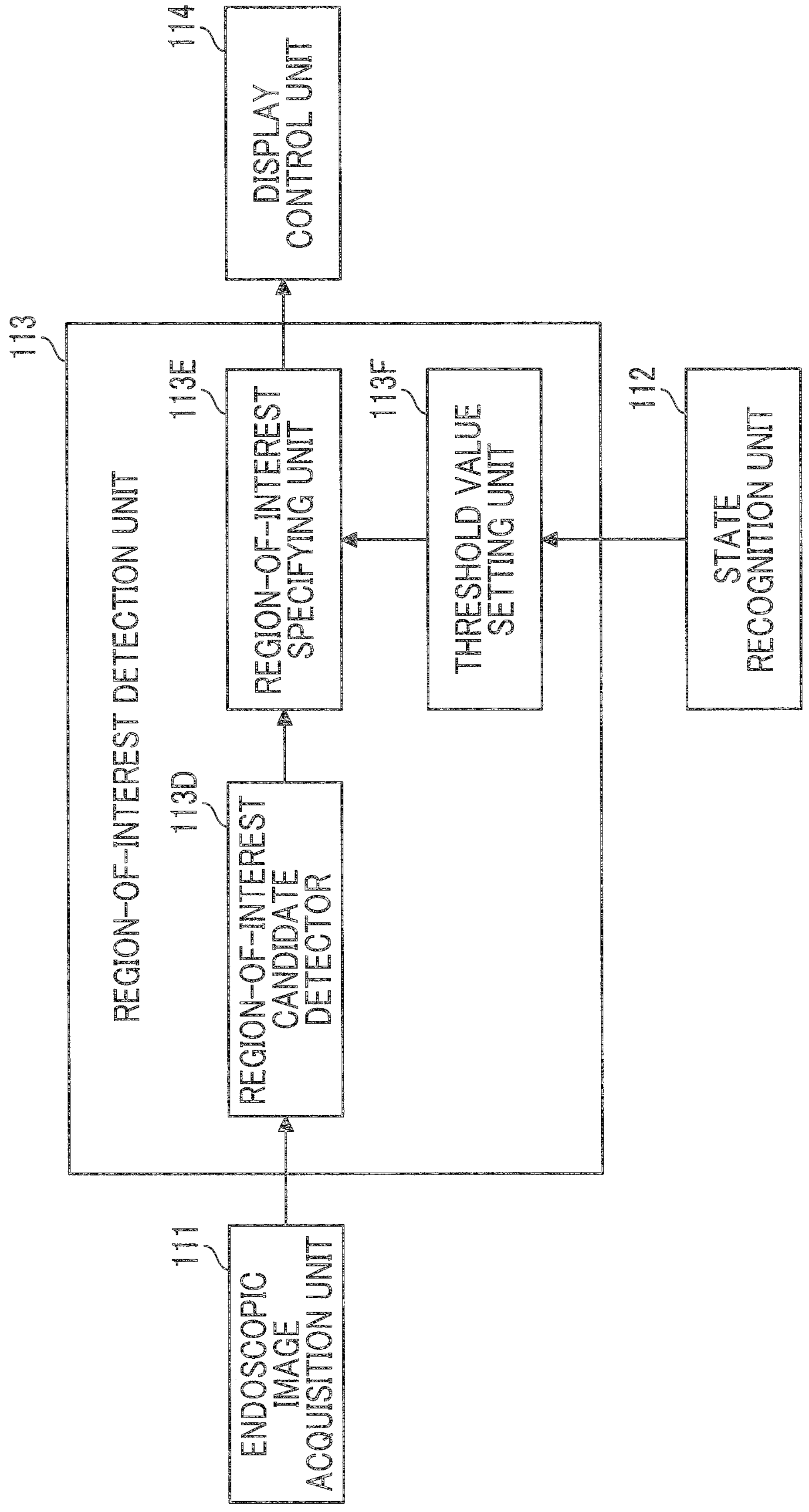
FIG. 9 is a block diagram of functions of a region-of-interest detection unit.

FIG. 9 is a block diagram of functions of the region-of-interest detection unit.

As illustrated in FIG. 9, the region-of-interest detection unit 113 of the present embodiment has functions of a region-of-interest candidate detector 113D, a region-of-interest specifying unit 113E, and a threshold value setting unit 113F.

The region-of-interest candidate detector 113D performs processing of detecting a region-of-interest candidate from the endoscopic image. The region-of-interest candidate detector 113D is configured by a trained model, and detects a region-of-interest candidate with a confidence level. The confidence level is a degree of probability indicating that the region-of-interest candidate is the region of interest. Therefore, the region-of-interest candidate detector 113D calculates the confidence level of all the detected region-of-interest candidates and performs the detection processing.

The region-of-interest specifying unit 113E extracts the region-of-interest candidate of which the confidence level is equal to or greater than a threshold value, from among the region-of-interest candidates detected by the region-of-interest candidate detector 113D, and specifies the region of interest.

The threshold value setting unit 113F sets the threshold value to be used in the region-of-interest specifying unit 113E. The threshold value setting unit 113F sets the threshold value according to the recognition result of the state of the examination target organ by the state recognition unit 112.

For example, in the gastric endoscopy, in a case where the pylori infection state of the stomach is recognized and the detection criterion is set according to the recognition result thereof, the threshold value is set according to the recognition result of the pylori infection state of the stomach. Specifically, in the case of the pylori positive (currently infected), a first threshold value is set, and in the case of the pylori negative (uninfected), a second threshold value is set.

In a case where the state after pylori eradication (eradicated) is also recognized, the threshold value (third threshold value) corresponding to the state after the pylori eradication is prepared.

Here, the second threshold value set in the case of the pylori negative is set to a relatively lower value than the first threshold value set in the case of the pylori positive (first threshold value>second threshold value). That is, the detection sensitivity in the case of the pylori negative is relatively higher than the detection sensitivity in the case of the pylori positive, thereby making it easier to detect the region of interest. Generally, the pylori-negative stomach has features that the surface of the mucous membrane thereof is smooth, glossy, and shiny. On the other hand, the pylori-positive stomach has features that the entire mucous membrane thereof is red, and mucus is white, impure, and viscous. Therefore, in a case where the detection is performed using the same criterion, the region of interest is more likely to be detected in the pylori-positive stomach than the pylori-negative stomach, and thus concern about erroneous detection is increased. That is, concern that a normal region is recognized as the region of interest is increased. Therefore, the erroneous recognition is suppressed by setting the second threshold value set in the case of the pylori negative to a relatively lower value than the first threshold value set in the case of the pylori positive.

Note that, in a case where the state after the pylori eradication is also recognized, the third threshold value set in the case after the pylori eradication is set to the same value as the first threshold value, or set to a value higher than the second threshold value and lower than the first threshold value. That is, the third threshold value is set to satisfy the relationships of first threshold value≥third threshold value and third threshold value>second threshold value.

In the present embodiment, the processing of setting the threshold value is an example of processing of setting the detection criterion for the region of interest.

Hereinafter, the operation of the endoscopic image processing device 100 of the present embodiment will be described using a case of performing gastric endoscopy as an example. Note that, here, a case where a threshold value is set depending on whether the pylori infection state of the stomach is positive or negative will be described as an example.

Figure 10:
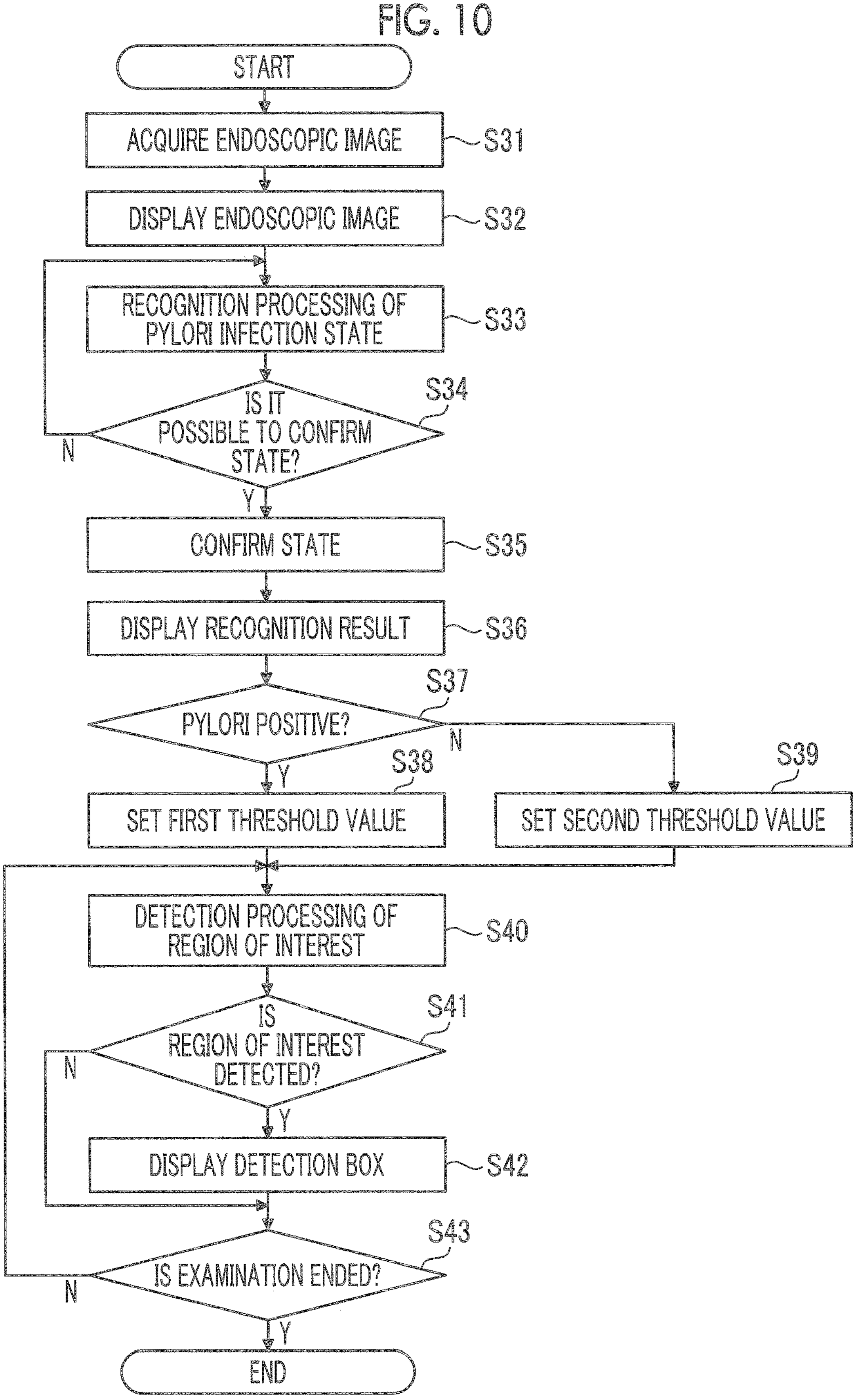
FIG. 10 is a flowchart illustrating a procedure of processing of detecting a region of interest from an endoscopic image.

FIG. 10 is a flowchart illustrating a procedure of processing of detecting the region of interest from the endoscopic image.

In a case where an examination starts, the images (endoscopic images) captured in chronological order by the endoscope 10 are sequentially output from the processor device 30 and taken into the endoscopic image processing device 100. That is, time-series endoscopic images are sequentially acquired (Step S31). The acquired endoscopic image is displayed on the display device 50 (Step S32).

In a case where the endoscopic image is acquired, recognition processing of the pylori infection state is performed on the acquired endoscopic image (Step S33). The recognition processing is sequentially performed on each of the endoscopic images acquired in chronological order.

In a case where the recognition processing is performed, it is determined whether or not the pylori infection state of the subject can be confirmed from the recognition processing result (Step S34). In a case where it is determined that the pylori infection state can be confirmed, the pylori infection state is confirmed (Step S35). That is, the pylori positive or the pylori negative is confirmed. In a case where the pylori infection state is confirmed, the recognition result is displayed on the display device 50 (Step S36).

In addition, in a case where the pylori infection state is confirmed, it is determined whether or not the confirmed recognition result is the pylori positive (Step S37). Then, a threshold value to be used in the case of detecting the region of interest is set on the basis of the determination result thereof. Specifically, in a case where the confirmed recognition result is the pylori positive, the first threshold value is set (Step S38). On the other hand, in a case where the confirmed recognition result is the pylori negative, the second threshold value is set (Step S39).

After the threshold value is set, the detection processing of the region of interest is performed on the basis of the set threshold value (Step S40). Specifically, in the case of the pylori positive, the region-of-interest candidate of which the confidence level is equal to or greater than the first threshold value is extracted from among the detected region-of-interest candidates, and is output as the detection result of the region of interest. On the other hand, in the case of the pylori negative, the region-of-interest candidate of which the confidence level is equal to or greater than the second threshold value is extracted from among the detected region-of-interest candidates, and is output as the detection result of the region of interest.

It is determined whether or not the region of interest is detected as a result of the detection processing of the region of interest (Step S41). In a case where the region of interest is detected, the detection box B is displayed by being superimposed on the endoscopic image Im that is being displayed on the display device 50 (Step S42).

Then, it is determined whether or not the examination is ended (Step S43). In a case where the examination is ended, the processing is ended. In a case where the examination is continuing, the detection processing of the region of interest from the endoscopic image is continued (Step S40).

As described above, according to the endoscopic image processing device of the present embodiment, in a case where the region of interest is detected from the endoscopic image using a single detector (region-of-interest candidate detector), the threshold value to be used for the detection is switched depending on the pylori infection state of the stomach. Accordingly, even in a case where the region of interest is detected by a single detector, the region of interest can be detected appropriately.

The endoscopic image processing device according to the first embodiment has the advantage of being able to optimize the detector depending on the state of the organ, thereby realizing more accurate detection.

On the other hand, since a single detector is used, the endoscopic image processing device of the present embodiment has the advantage of reducing the cost of collecting the training data for model construction.

Note that each modification example described in the first embodiment can also be applied to the present embodiment as appropriate.

Other Embodiments

[Hardware Configuration]

The functions of the endoscopic image processing device are realized by various processors. The various processors include a CPU and/or a graphics processing unit (GPU) as a general-purpose processor executing a program and functioning as various processing units, a programmable logic device (PLD) as a processor of which the circuit configuration can be changed after manufacture, such as a field-programmable gate array (FPGA), and a dedicated electrical circuit as a processor having a circuit configuration designed exclusively for executing specific processing such as an application-specific integrated circuit (ASIC). The program is synonymous with software.

One processing unit may be configured by one processor among these various processors, or may be configured by two or more same or different kinds of processors. For example, one processing unit may be configured by a plurality of FPGAs, or by a combination of a CPU and an FPGA. Further, a plurality of processing units may be configured by one processor. As an example where a plurality of processing units are configured by one processor, first, there is a form where one processor is configured by a combination of one or more CPUs and software as typified by a computer used in a client, a server, or the like, and this processor functions as a plurality of processing units. Second, there is a form where a processor fulfilling the functions of the entire system including a plurality of processing units via one integrated circuit (IC) chip as typified by a system-on-chip (SoC) or the like is used. In this manner, various processing units are configured by using one or more of the above-described various processors as hardware structures.

EXPLANATION OF REFERENCES

1: endoscope system
10: endoscope
20: light source device
30: processor device
31: endoscope control unit
32: light source control unit
33: image processing unit
34: input control unit
35: output control unit
40: input device
50: display device
100: endoscopic image processing device
111: endoscopic image acquisition unit
112: state recognition unit
112A: state recognizer
112B: state confirmation unit
113: region-of-interest detection unit
113A: first detector
113B: second detector
113C: detector setting unit
113D: region-of-interest candidate detector
113E: region-of-interest specifying unit
113F: threshold value setting unit
114: display control unit
A1: main display region
A2: secondary display region
B: detection box
IP: information on recognition result
Im: endoscopic image
X: region of interest
S11 to S23: procedure of processing of detecting region of interest from endoscopic image
S31 to S43: procedure of processing of detecting region of interest from endoscopic image

What is claimed is:

1. An endoscopic image processing device that processes an endoscopic image, the endoscopic image processing device comprising:

a processor, wherein the processor acquires the endoscopic image, recognizes a state of an organ as an examination target from the acquired endoscopic image, wherein the state of the organ is whether the organ has an infection detected by a trained model, sets a first detection criterion for a region of interest according to a recognition result of the state of the organ not showing the infection in the organ, sets a second detection criterion for the region of interest according to a recognition result of the state of the organ showing the infection in the organ, and detects a lesion from the region of interest from the endoscopic image on the basis of the set detection criterion.

2. The endoscopic image processing device according to claim 1, wherein the processor recognizes the state of the organ from the endoscopic image in which a specific region of the organ is imaged.

3. The endoscopic image processing device according to claim 1, wherein the processor recognizes the state of the organ from a plurality of endoscopic images in which different regions of the organ are imaged.

4. The endoscopic image processing device according to claim 1, wherein the endoscopic image used for recognizing the state of the organ is the endoscopic image in which a relatively wider range than the endoscopic image used for detecting the region of interest is imaged.

5. The endoscopic image processing device according to claim 1, wherein the processor recognizes the state of the organ by recognizing a state regarding histological abnormalities in a mucous membrane from the endoscopic image.

6. The endoscopic image processing device according to claim 1, wherein the processor acquires a plurality of endoscopic images captured in chronological order, recognizes the state of the organ showing the infection from a first endoscopic image among the plurality of endoscopic images, and detects the lesion in the region of interest from a second endoscopic image different from the first endoscopic image, among the plurality of endoscopic images in response to recognizing the infection for the state of the organ.

7. The endoscopic image processing device according to claim 6, wherein the processor determines whether or not the recognition result of the state of the organ recognized from a plurality of first endoscopic images satisfies a specific condition, confirms the recognition result of the state of the organ in a case where the recognition result of the state of the organ recognized from the plurality of first endoscopic images satisfies the specific condition, and fixes setting of the detection criterion based on the confirmed recognition result of the state of the organ.

8. The endoscopic image processing device according to claim 6, wherein the second endoscopic image is the endoscopic image captured temporally later than the first endoscopic image.

9. The endoscopic image processing device according to claim 1, wherein the processor displays information regarding the endoscopic image and the state of the organ recognized from the endoscopic image on a display device.

10. The endoscopic image processing device according to claim 1, wherein the processor notifies of a detection result of the region of interest in a different mode according to setting of the detection criterion.

11. The endoscopic image processing device according to claim 10, wherein the processor notifies of the endoscopic image to be displayed on a display device by surrounding the detected region of interest with a frame, and displays the frame in a display aspect according to the setting of the detection criterion.

12. The endoscopic image processing device according to claim 1, wherein the processor detects the region of interest from the endoscopic image using a trained model, and sets the trained model to be used for detecting the region of interest, according to the recognition result of the state of the organ.

13. The endoscopic image processing device according to claim 1, wherein the processor detects region-of-interest candidates from the endoscopic image by calculating a confidence level indicating probability, detects the region-of-interest candidate of which the confidence level is equal to or greater than a threshold value, from among the detected region-of-interest candidates, as the region of interest, and sets the threshold value according to the recognition result of the state of the organ.

14. The endoscopic image processing device according to claim 5, wherein the processor recognizes the state of the organ by recognizing a state regarding inflammation and/or atrophy of the mucous membrane as the state regarding the histological abnormalities in the mucous membrane.

15. The endoscopic image processing device according to claim 14, wherein the processor recognizes a state regarding *pylori* infection of a stomach as the state of the organ.

16. The endoscopic image processing device according to claim 15, wherein the processor recognizes uninfected, currently infected, and eradicated states as the state regarding the pylori infection of the stomach.

17. The endoscopic image processing device according to claim 16, wherein in a case where the recognition result of the state regarding the *pylori* infection of the stomach indicates the uninfected state, the processor sets the detection criterion relatively lower than in a case where the recognition result indicates the currently infected state and/or the eradicated state.

18. The endoscopic image processing device according to claim 14, wherein the processor recognizes a state regarding Barrett's esophagus of an esophagus.

19. The endoscopic image processing device according to claim 14, wherein the processor recognizes a state regarding an inflammatory bowel disease of a large intestine as the state of the organ.

20. The endoscopic image processing device according to claim 1, wherein the processor recognizes the state of the organ by dividing the state into three or more states, and sets the detection criterion according to the recognized state of the organ.

21. The endoscopic image processing device according to claim 1, wherein the processor acquires information on a light source type, and sets the detection criterion according to the recognition result of the state of the organ and the light source type.

22. An endoscopic image processing method of performing processing of detecting a region of interest from an endoscopic image using a trained model, the endoscopic image processing method comprising:

acquiring the endoscopic image;

recognizing a state of an organ as an examination target from the endoscopic image, wherein the state of the organ is whether the organ has an infection detected by the trained model;

setting a first detection criterion for the region of interest according to a recognition result of the state of the organ not showing the infection in the organ;

setting a second detection criterion for the region of interest according to a recognition result of the state of the organ showing the infection in the organ; and detecting a lesion from the region of interest from the endoscopic image on the basis of the set detection criterion.

23. An endoscopic image processing method of performing processing of detecting region-of-interest candidates from an endoscopic image by calculating a confidence level indicating probability, and detecting the region-of-interest candidate of which the confidence level is equal to or greater than a threshold value, from among the detected region-of-interest candidates, as a region of interest, the endoscopic image processing method comprising:

acquiring the endoscopic image;

recognizing a state of an organ as an examination target from the endoscopic image, wherein the state of the organ is whether the organ has an infection by using a trained model;

setting the threshold value as a first threshold value for detecting the region of interest according to a recognition result of the state of the organ not showing the infection in the organ;

setting the threshold value as a second detection criterion for detecting the region of interest according to a recognition result of the state of the organ showing the infection in the organ; and detecting a lesion from the region of interest from the endoscopic image on the basis of the set detection criterion.

24. An endoscope system comprising:

an endoscope; and the endoscopic image processing device according to claim 1 that processes the endoscopic image captured by the endoscope.

* * * * *